United States Patent [19] … [11] Patent Number: 4,501,816
Molla … [45] Date of Patent: Feb. 26, 1985

[54] METHOD OF DETERMINING IMMUNOGLOBULIN LEVELS IN MAMMALS

[76] Inventor: Aberra Molla, 6700 E. Montview Blvd., Denver, Colo. 80207

[21] Appl. No.: 429,044

[22] Filed: Sep. 30, 1982

[51] Int. Cl.³ .................... G01N 33/50; G01N 33/68; G01N 21/82
[52] U.S. Cl. ........................................ 436/34; 436/87; 436/517
[58] Field of Search ............................ 436/517, 34, 87

[56] References Cited

U.S. PATENT DOCUMENTS

| | | | |
|---|---|---|---|
| 3,716,336 | 2/1973 | Parekh | 23/230 B |
| 3,853,473 | 12/1974 | Morin et al. | 28/230 B |
| 3,890,099 | 6/1975 | Jung | 23/230 B |
| 3,912,610 | 10/1975 | Lou | 204/180 |

OTHER PUBLICATIONS

P. Liberg et al., Acta Vet. Scand., 16, 236–243, (1975).
Chemical Abstracts, 83:14407v, (1975).
Chemical Abstracts, 84:118168y, (1976).
Tennant B., et al., "Use of the Glutaraldehyde Coagulation Test for Detection of Hypogammaglobulinemia in Neonatal Calves", *JAVMA*, vol. 174, No. 8, pp. 848–853.
Molla, A., "Immunoglobulin Levels in Calves Fed Colostrum by Stomach Tube", *The Veterinary Record*, (Oct. 21, 1978).
Sandholm, M., "A Preliminary Report of a Rapid Method for the Demonstration of Abnormal Gamma-globulin Levels in Bovine Whole Blood", *Res. Vet. Sci.*, 1974, 17, (pp. 32–35).
Sandholm, M., et al., "Determination of γ-Globulin in Dog Serum by Glutaraldehyde", *J. Small Anim. Practice*, (1975), vol. 16, pp. 201–205.
A. Molla, "Estimation of Bovine Colostral Immunoglobulins by Refractometry", *The Veterinary Record*, (Jul. 12, 1980).
Sandholm, M., "Coagulation of Serum by Glutaraldehyde", *Clin. Biochem.*, vol. 9, No. 1, pp. 39–41, (1976).

*Primary Examiner*—Sidney Marantz
*Attorney, Agent, or Firm*—John E. Reilly

[57] ABSTRACT

A method of determining the presence of abnormal immunoglobulin levels in animal body fluids involves (a) forming a reaction mixture of a body fluid and an effective amount of an appropriate aldehyde; (b) timing the rate of reaction of the aldehyde to gel formation; and (c) comparing the rate of reaction of the reaction mixture to a known rate of reaction of a known mixture of the same aldehyde and body fluid containing a known quantity of an immunoglobulin.

12 Claims, No Drawings

4,501,816

METHOD OF DETERMINING IMMUNOGLOBULIN LEVELS IN MAMMALS

This invention relates to the detection of antibodies; and more particularly relates to a novel and improved method for the determination of immunoglobulin levels in body fluids.

BACKGROUND AND FIELD OF THE INVENTION

An important factor affecting the mortality rate among newborn animals is the presence of immunoglobulins among the newborn's physiological components. Immunoglobulins, in general, ward off illness and disease, and they must be present above certain threshold quantities in order to effectively function. Specifically, immunoglobulins are protein molecules by which the body defends itself against diseases. Due to the importance of mammalian immunoglobulins in the diagnosis, treatment and control of diseases, various qualitative and quantitative tests have been developed. Those in current use include the refractometer which estimates the total protein; sulfates and sulfites which assess the total globulin; electrophoresis which measures the total immunoglobulin; and radial immunodiffusion which assesses one type of immunoglobulin molecule at a time along with the various serological tests which measure the specific antibodies. Typically, the tests referred to are laborious and require the use of expensive laboratory instruments as well as highly trained personnel.

The primary source of immunoglobulins for the newborn is colostrum which, of course, is furnished by the animal's mother during nursing. Unfortunately, these nursing products often do not contain sufficient quantities of immunoglobulins to meet or exceed the threshold requirements. Unless these deficiencies are noted early during the first few hours in the newborn's life, and the diet is supplemented with appropriate additives, the newborn can succumb to illness or disease. Unfortunately, there is no simple test for assessing immunoglobulin levels in colostrum, milk or their whey under field and laboratory conditions.

Again, present techniques for detection of such deficiencies usually require rather sophisticated equipment, extended time periods, and body fluids which only are indirectly available (e.g., through centrifugation and separation) from the animal sample to be tested. Previously, aldehydes, such as, glutaraldehyde have been employed as reagents in testing immunoglobulin levels in serum. However, attempts to employ aldehydes in testing immunoglobulin levels in body fluids, such as, blood and plasma which have not been broken down into components of the fluids have been unsuccessful, principally because the aldehydes have not been used in sufficient concentrations to act as an anticoagulant and this was not known prior to my invention. Because of these limitations, it has been impractical in the past to perform the tests, especially if the newborns are, for example, farm animals that cannot be conveniently taken to a veterinary hospital or cannot be tested at the site of birth or sale; and without testing can result in death. Representative approaches which have been taken in the past are disclosed in U.S. Pat. No. 3,912,610 to Lou and which is directed to the use of a dilute glutaraldehyde in electroquantitative determination of proteins. The rate of reaction of dilute glutaraldehyde with immunoglobulins for assessing immunoglobulins in the serum of various animals is discussed in an article entitled "Use of the Glutaraldehyde Coagulation Test for Detection of Hypogammaglobulinemia in Neonatal Calves", by Tennant, B., DVM; JAVMA, Vol. 174, No. 8, Apr. 15, 1979.

A need exists for a simple convenient method and reagent which can be used in the field or in the laboratory for the determination of the presence of adequate immunoglobulin levels in samples from newborn animals and humans or in the food which they ingest and which method can be practiced and levels tested without the requirement of specialized knowledge or medical expertise. Unlike this invention which is useful in identifying and correcting the problem, past methods are technically limited to diagnosis in the laboratory or hospital.

SUMMARY OF THE INVENTION

The subject of the instant invention is a semi-quantitative method of determining immunoglobulin in animal body fluids. The method comprises: (a) forming a reaction mixture of a body fluid and an effective amount of an appropriate aldehyde; (b) timing the rate of reaction of the aldehyde to gel formation; and (c) comparing the rate of reaction of the reaction mixture to a known rate of reaction of a known mixture of the same aldehyde and body fluid containing a known quantity of an immunoglobulin.

The body fluids include colostrum, colostral whey, milk, milk whey and mixtures thereof, as well as whole blood, with or without anticoagulant, blood serum, plasma, urine, cerebrospinal fluid and the like. Most important is recognition of the ability to determine immunoglobulin levels without necessity of separation into components; and, in the case of blood, to obviate the use of an anticoagulant. The preferred aldehyde is glutaraldehyde, but any aldehyde as would be recognized by the skilled artisan can be employed so long as its function yields utility in the method herein disclosed.

It is to be noted that certain body fluids, such as, commercially sold cows' milk, should be free from excess immunoglobulins, and that the method herein disclosed therefore can be employed not only for the detection of immunoglobulins, but also for their absence.

The term "reaction mixture" as used herein means a mixture whose pH, temperature, reactant concentrations and the like are favorable for the reaction to occur if a sufficient quantity of an immunoglobulin is present in the mixture. As will be apparent below, the method here disclosed finds utility for testing body fluids as secreted or excreted directly by the animal, as well as for testing subsequently separated components of such fluids.

DETAILED DESCRIPTION OF THE PREFERRED EMBODIMENTS

In accordance with the present invention, it is possible to determine the immunoglobulin level from the rate of reaction of certain aldehydes with various body fluids. In other words, when the aldehyde and proteins in the body fluids react, a reaction product resulting in gelling takes place at a definite rate. The major protein which results in gelling is the immunoglobulin so that when a predetermined concentration of aldehyde is reacted with a given volume of the body fluid, the gelling time is inversely related to the immunoglobulin concentration and therefore can be used for estimating the immunoglobulin concentration. As earlier related, primary sources of immunoglobulins for a newborn animal are the colostrum and colostral whey secreted as a nursing product by the animal's mother. Consequently, determination of immunoglobulin levels, for example, from the mother's nursing product, provides a measurement of expected levels which will subsequently occur within the nursing newborn. An alternative approach is to test the blood of the newborn and correct this defect. In the examples which follow, the measurement of immunoglobulin levels is exemplified. These examples illustrate the rate of reaction, and define as the time period for gel formation caused by reaction of an immunoglobulin with an appropriate aldehyde, as a rapid and clinically significant indication of immunoglobulin present.

EXAMPLE 1

Colostrum was collected from about thirty-five dairy cows. The pool was preserved by freezing at −20° C. Colostral whey was prepared by incubating 10 ml of the colostrum at 37° C. for one hour after adding 0.1 ml of 10% rennet solution. Casein and fat were removed by centrifugation of the colostrum for 20 minutes at 3000 rpm. The colostrum pool contained 69% whey and the immunoglobulin as determined by refractometer and cellulose acetate membrane electrophoresis was 8.2 g/100 ml whey. The total immunoglobulin determined by single radial immunodiffusion was 9.44 g/dl whey.

Two milliliters of colostrum at room temperature were placed in a 10 ml glass tube to which was then added 100 microliters of a 25% glutaraldehyde solution which by weight is 25 milligrams of glutaraldehyde. This concentrated glutaraldehyde solution is a stock solution available from Eastman Kodak Company, Rochester, N.Y. Immediately after the addition of the glutaraldehyde solution, a stopper was placed on the tube and the tube was quickly inverted three times to mix the solutions. The end of the mixing was considered as zero time. Thereafter, the tube was tilted every 30 seconds and inverted every 60 seconds. A positive gelling time of 2.5 minutes was recorded. "Positive gelling time" is defined as the time required to reach that condition where no part of the fluid or the mass within the tube moves upon inverting the tube. Total protein of this colostrum sample was 3.8 g/dl after completion of the reaction and centrifugation.

EXAMPLES 2 TO 7

In the same manner as in Example 1, various reaction mixtures were prepared wherein the amounts of glutaraldehyde in each was varied. The results obtained in Examples 2 to 7 are shown in Table I which follows:

TABLE I

| Example No. | 2 | 3 | 4 | 5 | 6 | 7 |
|---|---|---|---|---|---|---|
| 25% Glutaraldehyde, μl | 25 | 50 | 75 | 150 | 200 | 300 |
| Glutaraldehyde concentration mg | 6.25 | 12.5 | 18.75 | 37.5 | 50 | 75 |
| Colostrum, ml | 2 | 2 | 2 | 2 | 2 | 2 |
| Gel-Time, minutes | >30.0 | 6.0 | 3.5 | 2.0 | 1.5 | 1.0 |
| Total Protein, g/dl | >15.0 | 3.1 | 3.4 | 4.0 | 4.5 | 5.0 |

It is to be observed from Table I that the concentration of glutaraldehyde in the reaction mixture has a marked effect on the rate of reaction or gel time; and, where the concentration is at levels of 12.5 mg or less, the reaction rate is greatly decreased. Thus, an effective concentration of glutaraldehyde would require a minimum of 12.5 mg while optimum results were obtained where the concentration was 25 mg or more. In tests performed on blood, not only is gel time substantially reduced but the ability of the aldehyde reagent to act as an anticoagulant and to inactivate the fibrinogen was greatly increased, and very much the same results were achieved as for the colostrum outlined above. Tests on blood without anticoagulant were performed within one minute of drawing of the blood from the animal and thus before clotting took place.

EXAMPLES 8 TO 14

In the same manner as in Examples 1 to 7, except at a temperature of 13° C., various reaction mixtures were prepared wherein the colostrum amount remained at 2 ml while the glutaraldehyde was varied. Table II, below, shows the results obtained.

TABLE II

| Example No. | 8 | 9 | 10 | 11 | 12 | 13 | 14 |
|---|---|---|---|---|---|---|---|
| 25% Glutaraldehyde, μl | 25 | 50 | 75 | 100 | 150 | 200 | 300 |
| Glutaraldehyde concentration mg | 6.25 | 12.5 | 18.75 | 25 | 37.5 | 50 | 75 |
| Colostrum, ml | 2 | 2 | 2 | 2 | 2 | 2 | 2 |
| Gel-Time, minutes | 120 | 10 | 8 | 6 | 4 | 3 | 2 |
| Total Protein, g/dl | >15.0 | 3.1 | 3.4 | 3.8 | 4.0 | 4.6 | 5.0 |

From the results shown in Examples 1 to 14, above, it is evident that the effective amount of glutaraldehyde by weight to colostrum by volume is from about 6.25 mg/ml to about 37.5 mg/ml in the reaction mixture. Total effective concentrations in excess of 37.5 mg/ml, although greatly accelerating reaction or gel-time, does not as accurately establish a differentiation between samples with high and low immunoglobulin levels. It is to be noted that the immunoglobulin level in the colostrum used in Examples 1 to 14 is adequate for proper nutrition of a newborn calf. Thus, a gel time generally equivalent to those times shown in Examples 1 to 14 experienced in testing the colostrum of a nursing mother particularly shows that the nursing products are adequate for a newborn animal. It has been found that the temperature at which testing is performed is not critical so long as the range of temperature is not below about 12° C. or above about 75° C. As is seen in the results of Tables I and II, however, gel time is affected by temperature. Therefore, when comparing test results to standardized results, it is necessary to make certain that similar temperature values and other variables have been observed throughout. As to pH of the reaction mixture, it has been found that pH values are not critical so long as pH is in the range of from about 3 to about 12.

As is known in the art, the pH of body fluids is within this range; but optional reaction takes place at a pH of 3.9 to 5.7.

EXAMPLES 15 TO 20

To illustrate the reaction between glutaraldehyde and colostral whey, the colostral whey obtained as described in Example I and combined with physiological saline solution was reacted in various concentrations of 50 microliters of the glutaraldehyde solution. Fifty microliters of the 25% glutaraldehyde solution is equivalent to 12.5 mg of glutaraldehyde. Table III, below, shows the results of this experimentation:

TABLE III

| Example No. | 15 | 16 | 17 | 18 | 19 | 20 |
|---|---|---|---|---|---|---|
| Whey, ml | 0.25 | 0.50 | 0.75 | 1.00 | 1.25 | 1.50 |
| Physiological Saline Solution, ml | 1.75 | 1.50 | 1.25 | 1.00 | 0.75 | 0.50 |
| Total Protein, g/dl | 1.5 | 2.3 | 3.7 | 5.4 | 7.1 | 8.5 |
| Gel-time, minues | 120 | 10 | 9 | 6 | 5 | 4 |

As evident from the results shown in Table III, the effective amounts of glutaraldehyde by weight to colostral whey by volume varies from about 6.25 mg/ml to about 25.0 mg/ml in the reaction mixture. As in the colostrum of Examples 1 to 14, the undiluted colostral whey or its colostrum used in Examples 15 to 20 is nutritionally adequate for a newborn calf. Thus, generally equivalent gel times found in the nursing products of a newborn's mother will quickly show that the newborn animal is receiving immunologically adequate food.

EXAMPLES 21 AND 22

As earlier related, certain body fluids, such as, commercially sold milk, should not have excess immunoglobulins present. Concurrently, if they are present, their detection is most important. Table IV, below, shows the results, shown in Example 21, of the addition of glutaraldehyde to milk with traces of immunoglobulins. Conversely, Example 22 shows the results of adding glutaraldehyde to a milk/colostrum mixture, said colostrum being that which was obtained in Example I.

TABLE IV

| Example No. | 21 | 22 |
|---|---|---|
| 25% Glutaraldehyde, μl 25 (mg) | 100 | 100 |
| Colostrum, ml | 0 | 0.50 |
| Milk, ml | 2 | 1.50 |
| Gel-Time | >30 minutes | 4 minutes |

As is evident from Table IV, the addition of glutaraldehyde to a milk product will quickly show the presence or absence of immunoglobulins.

The precise reaction of an aldehyde and an immunoglobulin is not known. However, most authorities agree that the amino groups of the immunoglobulin molecule, the protein molecule, are involved. Proteins with basic isoelectric points readily react, while those with acidic isoelectric points also compete for the aldehyde. When high concentrations of glutaraldehyde, for example, and immunoglobulins react under a given controlled condition, the immunoglobulins are polymerized, resulting in a solidification or gelling of the watery biological fluid at a constant rate. This rate is primarily dependent upon concentrations of the aldehyde and the immunoglobulin. However, the rate of reaction is affected by temperature, pH, volume of solution, concentration of the immunoglobulin as well as concentration of other proteins in the sample, the water content of the sample, the volume of the container in which the test is run, type of biological fluid, and the age and species of the source of the test sample. Therefore, it is important to approximate the composition of a known mixture to which the test mixture is compared. The method here disclosed for determining the presence of an immunoglobulin has as its objective the reporting of the general presence of abnormal levels of immunoglobulin. Its primary goal is speed and convenience more than to provide precise quantitative data.

In addition to measuring immunoglobulin levels in body fluids which are secreted, the instant method of determining the presence of an immunoglobulin can be utilized for the determination of immunoglobulin levels in whole blood, blood serum and plasma. Because a reaction occurs between immunoglobulins and an appropriate aldehyde, the presence of immunoglobulins in other body fluids, such as urine and cerebrospinal fluid, can be determined by the addition of an appropriate aldehyde, such as, glutaraldehyde, to said fluid as in Examples 21 and 22. The Examples 23 to 25, below, which represent a compilation of results of experimental data illustrate, respectively, the results obtained utilizing whole blood, blood serum and plasma.

EXAMPLE 23

According to the mixing technique as described in Example 1, two milliliters of whole blood from a hypergammaglobulinemic calf were placed in one tube, and two milliliters of whole blood from a hypogammaglobulinemic calf were placed in a second tube. To each of these tubes, 0.1 ml of 25% glutaraldehyde solution was added. The quantity by weight of glutaraldehyde is 25 mg. The tube containing the hypergammaglobulinemic blood showed gelling within two minutes; the tube containing the hypogammaglobulinemic blood did not show gelling within thirty minutes.

EXAMPLE 24

Using the same techniques as in Example 23, except for substituting serum in place of whole blood, one milliliter of serum from a calf with sufficient immunoglobulin levels gels within two minutes; while one ml of serum from a calf having insufficient immunoglobulin levels does not gel within thirty minutes.

EXAMPLE 25

Using the same techniques as in Example 23, except for substituting plasma in place of whole blood, one milliliter from a calf with sufficient immunoglobulin levels gels within one and one-half minutes; while one ml of plasma from a calf having insufficient immunoglobulin levels does not gel within thirty minutes.

From the results shown in Examples 23 to 25, it is evident that the instant method can be employed in quickly determining the immunoglobulin levels in the body fluids so described. Additionally, and in relation to the measurement of immunoglobulins in whole blood and blood plasma, I have found that 1.25 mg of glutaraldehyde per ml blood acts as an anticoagulant. Concurrently, however, such reaction with an inactivation of fibrinogen and related clotting proteins does not cause gelling in the absence of a sufficient level of immunoglobulins. Thus, when practicing the instant method using whole blood, it is not necessary to first treat the blood with a separate anticoagulant. The test can also be used on blood with anticoagulant since the reaction is not seriously affected.

Following the precepts of the present invention, it can be appreciated that simple and rapid field tests can be performed to determine the presence of abnormal immunoglobulin levels in body fluids. Simply, this is done by extracting a small sample and placing it in a suitable container, such as, a test tube and introducing a predetermined concentration of glutaraldehyde. From the Tables and Examples given, the optimum concentration for a 1 or 2 milliliter sample of body fluid is on the order of 25% in a 100 microliter solution of glutaraldehyde; or, stated another way, would be 25 milligrams of glutaraldehyde for mixture with a 1 or 2 milliliter sample. The solution and test sample are mixed in the test tube by quickly shaking or inverting the tube and then timed. The tube is tilted every thirty seconds and inverted every minute for a few minutes or until gelling occurs. Positive gelling time is recorded in minutes when no part of the fluid or mass moves upon inverting the tube. The gel time can then be extrapolated or compared with standardized tests to indicate the immunoglobulin level in the fluid.

Examples 26 to 31 represent major characteristics of standardized positive field and laboratory test results with the use of 25 milligram glutaraldehyde. The statistical results were significantly different from those of the negatives.

TABLE V

| Example No.: | 26 | 27 | 28 | 29 | 30 | 31 |
|---|---|---|---|---|---|---|
| Test Sample | Colostrum | Colostral Whey | Blood | Serum in Blood | Serum | Plasma |
| Sample Volume, ml | 2 | 1 | 2 | — | 1 | 1 |
| Gel-time, minutes | ≦2 | ≦0.5 | ≦2 | ≦2 | ≦2 | ≦1.5 |
| Total Protein g/dl | >7.7 | >12.1 | >3.1 | >5.0 | >5.2 | >4.6 |
| Immune Globulin g/dl | >5.3 | >8.4 | >0.5 | >0.8 | >1.1 | >0.6 |
| Immunoglobulin g/dl | >5.9 | >10.4 | >0.9 | >1.6 | >2.2 | >1.4 |
| Plasma Protein g/dl | >14.0 | — | >3.4 | >5.4 | >5.7 | >5.2 |

Since the protein concentrations differ in various body fluids, the use of the test on different fluids has potential disease diagnostic value.

Among the reactions which can verify or be used for assessing immunoglobulin levels are a number of physico-chemical changes including refractometric, turbidametric, precipitation, supernatant volume, viscosity, electrophoretic, immunoelectrophoretic, colorimetric, total protein, pH and other changes. Gelling which is one of these time dependent changes was preferred due to its uniformity, stability and simplicity.

It is to be understood that the above examples are illustrative and not limiting, and that the scope of the instant invention is defined in the claims which now follow.

I claim:
1. A method of determining immunoglobulin levels in the body fluids of a mammal, said method comprising:
    (a) forming a reaction mixture of a body fluid and an aldehyde wherein the concentration of said aldehyde by weight to body fluid by volume is in excess of about 6.25 mg/ml and wherein said aldehyde is effective as a gelling agent;
    (b) determining the positive gelling time; and
    (c) comparing the positive gelling time of the reaction mixture to a known positive gelling time of a known mixture of the same aldehyde and body fluid containing a known quantity of an immunoglobulin.
2. The method of claim 1 wherein the body fluid is chosen from the group consisting of whole blood, blood serum, plasma, urine and cerebrospinal fluid.
3. The method of claim 1 wherein the body fluid is derived from an animal.
4. The method of claim 1 wherein the aldehyde is glutaraldehyde.
5. The method of claim 2 wherein the body fluid is whole blood and the concentration of glutaraldehyde is sufficient to act as an anticoagulant.
6. The method of claim 5, wherein the effective concentration of glutaraldeyde is on the order of 12.5 mg/ml to 25.0 mg/ml.
7. The method of claim 4 wherein the body fluid is chosen from the group consisting of colostrum, colostral whey, milk, milk whey and mixtures thereof.
8. The method of claim 7 wherein the body fluid is colostrum and wherein the effective amount of glutaraldehyde by weight to colostrum by volume is from about 6.25 mg/ml to about 37.5 mg/ml in the reaction mixture.
9. The method of claim 7 wherein the body fluid is colostral whey, and wherein the effective amount of glutaraldehyde by weight to colostral whey by volume is from about 6.25 mg/ml to about 25.0 mg/ml in the reaction mixture.
10. The method of determining immunoglobulin levels in the body fluids of an animal wherein said body fluids have not been separated into components comprising:
    (a) forming a reaction mixture of a body fluid and glutaraldehyde wherein the concentration of said glutaraldehyde by weight to body fluid by volume is in excess of about 6.25 mg/ml and wherein said glutaraldehyde is effective both as a gelling agent and an anticoagulant;
    (b) determining the positive gelling time; and
    (c) comparing the positive gelling time of the reaction mixture to a known positive gelling time of a known mixture of said glutaraldehyde and body fluid containing a known quantity of an immunoglobulin.
11. The method of claim 10 wherein the body fluid is selected from the group consisting of colostrum, colostral whey, milk, and mixtures thereof.
12. The method of claim 11 wherein the body fluid is colostrum and wherein the effective amount of glutaraldehyde by weight to colostrum by volume is from about 6.25 mg/ml to about 37.5 mg/ml in the reaction mixture.

* * * * *